US008445286B2

(12) United States Patent
Bair et al.

(10) Patent No.: US 8,445,286 B2
(45) Date of Patent: May 21, 2013

(54) FLOW CELL FOR A FLOW CYTOMETER SYSTEM

(75) Inventors: Nathaniel C. Bair, Ann Arbor, MI (US); Collin A. Rich, Ypsilanti, MI (US); Mark Robert Eadie, Ann Arbor, MI (US); Rebecca Ann Lehrmann, Ann Arbor, MI (US)

(73) Assignee: Accuri Cytometers, Inc., Ann Arbor, MI (US)

( * ) Notice: Subject to any disclaimer, the term of this patent is extended or adjusted under 35 U.S.C. 154(b) by 585 days.

(21) Appl. No.: 12/514,052

(22) PCT Filed: Nov. 7, 2007

(86) PCT No.: PCT/US2007/083991
§ 371 (c)(1),
(2), (4) Date: Jan. 19, 2010

(87) PCT Pub. No.: WO2008/058217
PCT Pub. Date: May 15, 2008

(65) Prior Publication Data
US 2010/0118298 A1    May 13, 2010

Related U.S. Application Data

(60) Provisional application No. 60/864,646, filed on Nov. 7, 2006.

(51) Int. Cl.
| G01N 33/48 | (2006.01) |
| G01N 35/08 | (2006.01) |
| G01N 21/00 | (2006.01) |
| G01N 33/00 | (2006.01) |
| G01N 35/00 | (2006.01) |

(52) U.S. Cl.
USPC ............... 436/52; 436/50; 422/62; 422/67; 422/68.1; 422/73; 422/81; 137/7; 137/12; 137/15.04

(58) Field of Classification Search
None
See application file for complete search history.

(56) References Cited

U.S. PATENT DOCUMENTS

| 3,347,273 A | 7/1960 | Russell |
| 3,061,128 A | 12/1968 | Hakim |
| 3,672,402 A | 6/1972 | Bloemer |
| 3,819,272 A | 6/1974 | Crozier et al. |
| 4,112,735 A | 9/1978 | McKnight |
| 4,138,879 A | 2/1979 | Liebermann |
| 4,371,786 A | 2/1983 | Kramer |
| 4,448,538 A | 5/1984 | Mantel |

(Continued)

FOREIGN PATENT DOCUMENTS

| EP | 466490 A | 1/1992 |
| EP | 1391611 A | 2/2004 |

(Continued)

*Primary Examiner* — Neil N Turk
(74) *Attorney, Agent, or Firm* — Jeffrey Schox

(57) ABSTRACT

The flow cytometer system of the preferred embodiment includes a flow cell body that functions to contain, protect, and align the components of the flow cytometer system; a flow channel, coupled to the flow cell body, that functions to conduct and focus sample fluid through an interrogation zone; and a sample injection probe, removably coupled to the flow cell body, that functions to provide a uniform flow of sample fluid to the flow channel. The flow cytometer system is preferably designed for the flow cytometer field. The flow cytometer system, however, may be alternatively used in any suitable environment and for any suitable reason.

19 Claims, 8 Drawing Sheets

U.S. PATENT DOCUMENTS

| | | |
|---|---|---|
| 4,559,454 A | 12/1985 | Kramer |
| 4,570,639 A | 2/1986 | Miodownik |
| 4,691,829 A | 9/1987 | Auer |
| 4,755,021 A | 7/1988 | Dyott |
| 4,790,653 A | 12/1988 | North, Jr. |
| 4,818,103 A | 4/1989 | Thomas et al. |
| 4,824,641 A | 4/1989 | Williams |
| 4,826,660 A | 5/1989 | Smith et al. |
| 4,844,610 A | 7/1989 | North, Jr. |
| 4,933,813 A | 6/1990 | Berger |
| 5,028,127 A | 7/1991 | Spitzberg |
| 5,040,890 A | 8/1991 | North, Jr. |
| 5,043,706 A | 8/1991 | Oliver |
| 5,083,862 A | 1/1992 | Rusnak |
| 5,138,868 A | 8/1992 | Long |
| 5,139,609 A | 8/1992 | Fields et al. |
| 5,150,037 A * | 9/1992 | Kouzuki ............... 324/71.4 |
| 5,150,313 A | 9/1992 | Van den et al. |
| 5,155,543 A | 10/1992 | Hirako |
| 5,204,884 A | 4/1993 | Leary et al. |
| 5,224,058 A | 6/1993 | Mickaels et al. |
| 5,230,026 A | 7/1993 | Ohta et al. |
| 5,270,548 A | 12/1993 | Steinkamp |
| 5,301,685 A * | 4/1994 | Guirguis ............... 600/573 |
| 5,308,990 A | 5/1994 | Takahashi et al. |
| 5,367,474 A | 11/1994 | Auer et al. |
| 5,374,395 A | 12/1994 | Robinson et al. |
| 5,395,588 A | 3/1995 | North, Jr. et al. |
| 5,403,552 A | 4/1995 | Pardikes |
| 5,466,946 A | 11/1995 | Kleinschmitt et al. |
| 5,469,375 A | 11/1995 | Kosaka |
| 5,539,386 A | 7/1996 | Elliott |
| 5,552,885 A | 9/1996 | Steen |
| 5,559,339 A | 9/1996 | Domanik et al. |
| 5,616,124 A | 4/1997 | Hague et al. |
| 5,684,480 A | 11/1997 | Jansson |
| 5,739,902 A | 4/1998 | Gjelsnes et al. |
| 5,797,430 A | 8/1998 | Becke et al. |
| 5,798,222 A | 8/1998 | Goix |
| 5,804,507 A | 9/1998 | Perlov et al. |
| 5,883,378 A | 3/1999 | Irish et al. |
| 5,920,388 A | 7/1999 | Sandberg et al. |
| 5,960,129 A | 9/1999 | Kleinschmitt |
| 5,981,180 A | 11/1999 | Chandler et al. |
| 6,016,376 A | 1/2000 | Ghaemi et al. |
| 6,039,078 A | 3/2000 | Tamari |
| 6,067,157 A | 5/2000 | Altendorf |
| 6,070,477 A | 6/2000 | Mark |
| 6,091,502 A | 7/2000 | Weigl et al. |
| 6,097,485 A | 8/2000 | Lievan |
| 6,108,463 A | 8/2000 | Herron et al. |
| 6,110,427 A | 8/2000 | Uffenheimer |
| 6,115,065 A | 9/2000 | Yadid-Pecht et al. |
| 6,139,800 A | 10/2000 | Chandler |
| 6,154,276 A | 11/2000 | Mariella, Jr. |
| 6,156,208 A | 12/2000 | Desjardins et al. |
| 6,181,319 B1 | 1/2001 | Fujita et al. |
| 6,183,697 B1 | 2/2001 | Tanaka et al. |
| 6,288,783 B1 | 9/2001 | Auad |
| 6,377,721 B1 | 4/2002 | Walt et al. |
| 6,382,228 B1 | 5/2002 | Cabuz et al. |
| 6,403,378 B1 | 6/2002 | Phi-Wilson et al. |
| 6,427,521 B2 | 8/2002 | Jakkula et al. |
| 6,431,950 B1 | 8/2002 | Mayes |
| 6,456,769 B1 | 9/2002 | Furusawa et al. |
| 6,469,787 B1 | 10/2002 | Meyer et al. |
| 6,473,171 B1 * | 10/2002 | Buttry et al. ............... 356/246 |
| 6,519,355 B2 | 2/2003 | Nelson |
| 6,522,775 B2 | 2/2003 | Nelson |
| 6,568,271 B2 | 5/2003 | Shah et al. |
| 6,587,203 B2 * | 7/2003 | Colon ............... 356/436 |
| 6,602,469 B1 | 8/2003 | Maus et al. |
| 6,636,623 B2 | 10/2003 | Nelson et al. |
| 6,675,835 B2 | 1/2004 | Gerner et al. |
| 6,694,799 B2 | 2/2004 | Small |
| 6,700,130 B2 | 3/2004 | Fritz |
| 6,710,871 B1 | 3/2004 | Goix |
| 6,718,415 B1 | 4/2004 | Chu |
| 6,778,910 B1 | 8/2004 | Vidal et al. |
| 6,809,804 B1 | 10/2004 | Yount et al. |
| 6,816,257 B2 | 11/2004 | Goix |
| 6,825,926 B2 | 11/2004 | Turner et al. |
| 6,852,284 B1 | 2/2005 | Holl et al. |
| 6,859,570 B2 | 2/2005 | Walt et al. |
| 6,869,569 B2 | 3/2005 | Kramer |
| 6,872,180 B2 | 3/2005 | Reinhardt et al. |
| 6,890,487 B1 | 5/2005 | Sklar et al. |
| 6,897,954 B2 | 5/2005 | Bishop et al. |
| 6,901,964 B2 | 6/2005 | Kippe et al. |
| 6,908,226 B2 | 6/2005 | Siddiqui et al. |
| 6,912,904 B2 | 7/2005 | Storm, Jr. et al. |
| 6,936,828 B2 | 8/2005 | Saccomanno |
| 6,941,005 B2 | 9/2005 | Lary et al. |
| 6,944,322 B2 | 9/2005 | Johnson et al. |
| 7,009,189 B2 | 3/2006 | Saccomanno |
| 7,012,689 B2 | 3/2006 | Sharpe |
| 7,019,834 B2 | 3/2006 | Sebok et al. |
| 7,024,316 B1 | 4/2006 | Ellison et al. |
| 7,061,595 B2 | 6/2006 | Cabuz et al. |
| 7,075,647 B2 | 7/2006 | Christodoulou |
| 7,105,355 B2 | 9/2006 | Kurabayashi et al. |
| 7,106,442 B2 | 9/2006 | Silcott et al. |
| 7,113,266 B1 | 9/2006 | Wells |
| 7,130,046 B2 | 10/2006 | Fritz et al. |
| 7,232,687 B2 | 6/2007 | Lary et al. |
| 7,262,838 B2 | 8/2007 | Fritz |
| 7,274,316 B2 | 9/2007 | Moore |
| 7,328,722 B2 | 2/2008 | Rich |
| 7,362,432 B2 | 4/2008 | Roth |
| 7,403,125 B2 | 7/2008 | Rich |
| 7,471,393 B2 | 12/2008 | Trainer |
| 7,520,300 B2 | 4/2009 | Rich |
| 7,628,956 B2 | 12/2009 | Jindo |
| 7,738,099 B2 | 6/2010 | Morrell |
| 7,739,060 B2 | 6/2010 | Goebel et al. |
| 7,776,268 B2 | 8/2010 | Rich |
| 7,780,916 B2 | 8/2010 | Bair et al. |
| 7,843,561 B2 | 11/2010 | Rich |
| 7,857,005 B2 | 12/2010 | Rich et al. |
| 7,903,706 B2 | 3/2011 | O'Shaughnessy et al. |
| 7,981,661 B2 | 7/2011 | Rich |
| 7,996,188 B2 | 8/2011 | Olson et al. |
| 8,017,402 B2 | 9/2011 | Rich |
| 8,031,340 B2 | 10/2011 | Rich et al. |
| 2001/0014477 A1 | 8/2001 | Pelc et al. |
| 2001/0039053 A1 | 11/2001 | Liseo et al. |
| 2002/0028434 A1 | 3/2002 | Goix et al. |
| 2002/0049782 A1 | 4/2002 | Herzenberg et al. |
| 2002/0059959 A1 | 5/2002 | Qatu et al. |
| 2002/0080341 A1 | 6/2002 | Kosaka |
| 2002/0123154 A1 | 9/2002 | Burshteyn et al. |
| 2002/0192113 A1 | 12/2002 | Uffenheimer et al. |
| 2003/0035168 A1 | 2/2003 | Qian et al. |
| 2003/0048539 A1 | 3/2003 | Oostman, Jr. et al. |
| 2003/0054558 A1 | 3/2003 | Kurabayashi et al. |
| 2003/0062314 A1 | 4/2003 | Davidson et al. |
| 2003/0072549 A1 | 4/2003 | Facer et al. |
| 2003/0078703 A1 | 4/2003 | Potts et al. |
| 2003/0129090 A1 | 7/2003 | Farrell |
| 2003/0134330 A1 | 7/2003 | Ravkin et al. |
| 2003/0148379 A1 | 8/2003 | Roitman et al. |
| 2003/0175157 A1 | 9/2003 | Micklash, II et al. |
| 2003/0202175 A1 | 10/2003 | van den Engh et al. |
| 2003/0211009 A1 | 11/2003 | Buchanan |
| 2003/0223061 A1 | 12/2003 | Sebok et al. |
| 2003/0235919 A1 | 12/2003 | Chandler |
| 2004/0031521 A1 | 2/2004 | Vrane et al. |
| 2004/0048362 A1 | 3/2004 | Trulson et al. |
| 2004/0112808 A1 | 6/2004 | Takagi et al. |
| 2004/0119974 A1 | 6/2004 | Bishop et al. |
| 2004/0123645 A1 | 7/2004 | Storm, Jr. et al. |
| 2004/0131322 A1 | 7/2004 | Ye et al. |
| 2004/0143423 A1 | 7/2004 | Parks et al. |
| 2004/0175837 A1 | 9/2004 | Bonne et al. |
| 2004/0197768 A1 | 10/2004 | Glencross |
| 2004/0201845 A1 | 10/2004 | Quist et al. |
| 2004/0246476 A1 | 12/2004 | Bevis et al. |

| Publication No. | Date | Inventor |
|---|---|---|
| 2005/0044110 A1 | 2/2005 | Herzenberg et al. |
| 2005/0047292 A1 | 3/2005 | Park et al. |
| 2005/0057749 A1 | 3/2005 | Dietz et al. |
| 2005/0069454 A1 | 3/2005 | Bell |
| 2005/0073686 A1 | 4/2005 | Roth et al. |
| 2005/0078299 A1 | 4/2005 | Fritz et al. |
| 2005/0105091 A1 | 5/2005 | Lieberman et al. |
| 2005/0162648 A1 | 7/2005 | Auer et al. |
| 2005/0163663 A1 | 7/2005 | Martino et al. |
| 2005/0195605 A1 | 9/2005 | Saccomanno et al. |
| 2005/0195684 A1 | 9/2005 | Mayer |
| 2005/0252574 A1 | 11/2005 | Khan et al. |
| 2006/0002634 A1 | 1/2006 | Riley et al. |
| 2006/0015291 A1 | 1/2006 | Parks et al. |
| 2006/0023219 A1 | 2/2006 | Meyer et al. |
| 2006/0161057 A1 | 7/2006 | Weber et al. |
| 2006/0177937 A1 | 8/2006 | Kurabayashi et al. |
| 2006/0219873 A1 | 10/2006 | Martin et al. |
| 2006/0280061 A1 | 12/2006 | Koreeda et al. |
| 2006/0281143 A1 | 12/2006 | Liu et al. |
| 2006/0286549 A1 | 12/2006 | Sohn et al. |
| 2007/0003434 A1 | 1/2007 | Padmanabhan et al. |
| 2007/0041013 A1 | 2/2007 | Fritz et al. |
| 2007/0096039 A1 | 5/2007 | Kapoor et al. |
| 2007/0124089 A1 | 5/2007 | Jochum et al. |
| 2007/0127863 A1 | 6/2007 | Bair et al. |
| 2007/0144277 A1 | 6/2007 | Padmanabhan et al. |
| 2007/0212262 A1 | 9/2007 | Rich |
| 2007/0224684 A1 | 9/2007 | Olson et al. |
| 2007/0243106 A1 | 10/2007 | Rich |
| 2008/0055595 A1 | 3/2008 | Olson et al. |
| 2008/0064113 A1 | 3/2008 | Goix et al. |
| 2008/0092961 A1 | 4/2008 | Bair et al. |
| 2008/0152542 A1 | 6/2008 | Ball et al. |
| 2008/0215297 A1 | 9/2008 | Goebel et al. |
| 2008/0228444 A1 | 9/2008 | Olson et al. |
| 2008/0246949 A1 | 10/2008 | Harris et al. |
| 2009/0104075 A1 | 4/2009 | Rich |
| 2009/0174881 A1 | 7/2009 | Rich |
| 2009/0201501 A1 | 8/2009 | Bair et al. |
| 2009/0202130 A1 | 8/2009 | George et al. |
| 2009/0216478 A1 | 8/2009 | Estevez-Labori |
| 2009/0257339 A1 | 10/2009 | Katayama |
| 2009/0260701 A1 | 10/2009 | Rich |
| 2009/0293910 A1 | 12/2009 | Ball et al. |
| 2010/0008204 A1 | 1/2010 | Bae et al. |
| 2010/0012853 A1 | 1/2010 | Parks et al. |
| 2010/0032584 A1 | 2/2010 | Dayong et al. |
| 2010/0119298 A1 | 5/2010 | Huang |
| 2010/0302536 A1 | 12/2010 | Ball et al. |
| 2010/0319469 A1 | 12/2010 | Rich |
| 2010/0319786 A1 | 12/2010 | Bair et al. |
| 2011/0008816 A1 | 1/2011 | Ball et al. |
| 2011/0058163 A1 | 3/2011 | Rich |
| 2011/0061471 A1 | 3/2011 | Rich et al. |
| 2011/0306031 A1 | 12/2011 | Rich |

FOREIGN PATENT DOCUMENTS

| | | |
|---|---|---|
| EP | 1396736 | 3/2004 |
| EP | 1521076 | 9/2004 |
| EP | 1521076 | 4/2005 |
| JP | 356169978 | 12/1981 |
| JP | 5913689 | 3/1984 |
| JP | 6353901 | 4/1988 |
| JP | 04-086546 | 3/1992 |
| JP | 6194299 A | 7/1994 |
| JP | 06221988 H | 12/1994 |
| JP | 7260084 A | 10/1995 |
| JP | 08201267 H | 8/1996 |
| JP | 09288053 H | 11/1997 |
| JP | 10-227737 | 8/1998 |
| JP | 2001050887 A | 2/2001 |
| JP | 2001170062 A | 6/2001 |
| JP | 2003262201 A | 9/2003 |
| JP | 200477484 | 3/2004 |
| WO | 9956052 | 11/1999 |
| WO | 0194914 | 12/2001 |
| WO | 2005017499 | 8/2004 |
| WO | WO /2005/017499 | 2/2005 |
| WO | 2005068971 A | 7/2005 |
| WO | 2005/073694 | 8/2005 |
| WO | 2005091893 A | 10/2005 |
| WO | 2006055722 A | 5/2006 |
| WO | 2007067577 A | 6/2007 |
| WO | 2007/100723 | 9/2007 |
| WO | 2007103969 A | 9/2007 |
| WO | 2007136749 A | 11/2007 |
| WO | 2008058217 A | 5/2008 |
| WO | 2010101623 A | 9/2010 |

* cited by examiner

FLOW CELL FOR A FLOW CYTOMETER SYSTEM

CROSS-REFERENCE TO RELATED APPLICATIONS

This application claims the benefit of U.S. Provisional Application No. 60/864,646 filed 7 Nov. 2006 and entitled "FLOW CELL FOR A FLOW CYTOMETER SYSTEM", which is incorporated in its entirety by this reference.

TECHNICAL FIELD

This invention relates generally to the flow cytometer field, and more specifically to a flow cytometer system with a flow cell body, a flow channel, and a sample injection probe.

BACKGROUND

A typical flow cell for a flow cytometer system, which includes a flow channel, is composed of multiple pieces of fused silica that must be individually cast or cut and later assembled. The typical flow channel is susceptible to clogs and bubbles. A clog, which prevents flow of the sample fluid, may be caused by sample debris, conjugated or clustered cells, or other substances inserted into the flow path of the flow cytometer. Bubbles may interfere with the optical interrogation of the sample as it passes through the interrogation zone. Both clogs and bubbles within the flow channel can render experimental data useless, which in turn leads to repetitive experiments, increased costs, and lost time associated with the maintenance and operation of the flow cytometer.

Thus, there is a need for a flow cell that provides for improved construction and integration of its component parts, as well as a flow cytometer system that reduces the likelihood of clogs and bubbles in the flow channel. This invention provides such an improved and useful flow cytometer.

DESCRIPTION OF THE PREFERRED EMBODIMENTS

The following description of the preferred embodiments of the invention is not intended to limit the invention to these preferred embodiments, but rather to enable any person skilled in the art of flow cytometry to make and use this invention.

Figure 1:
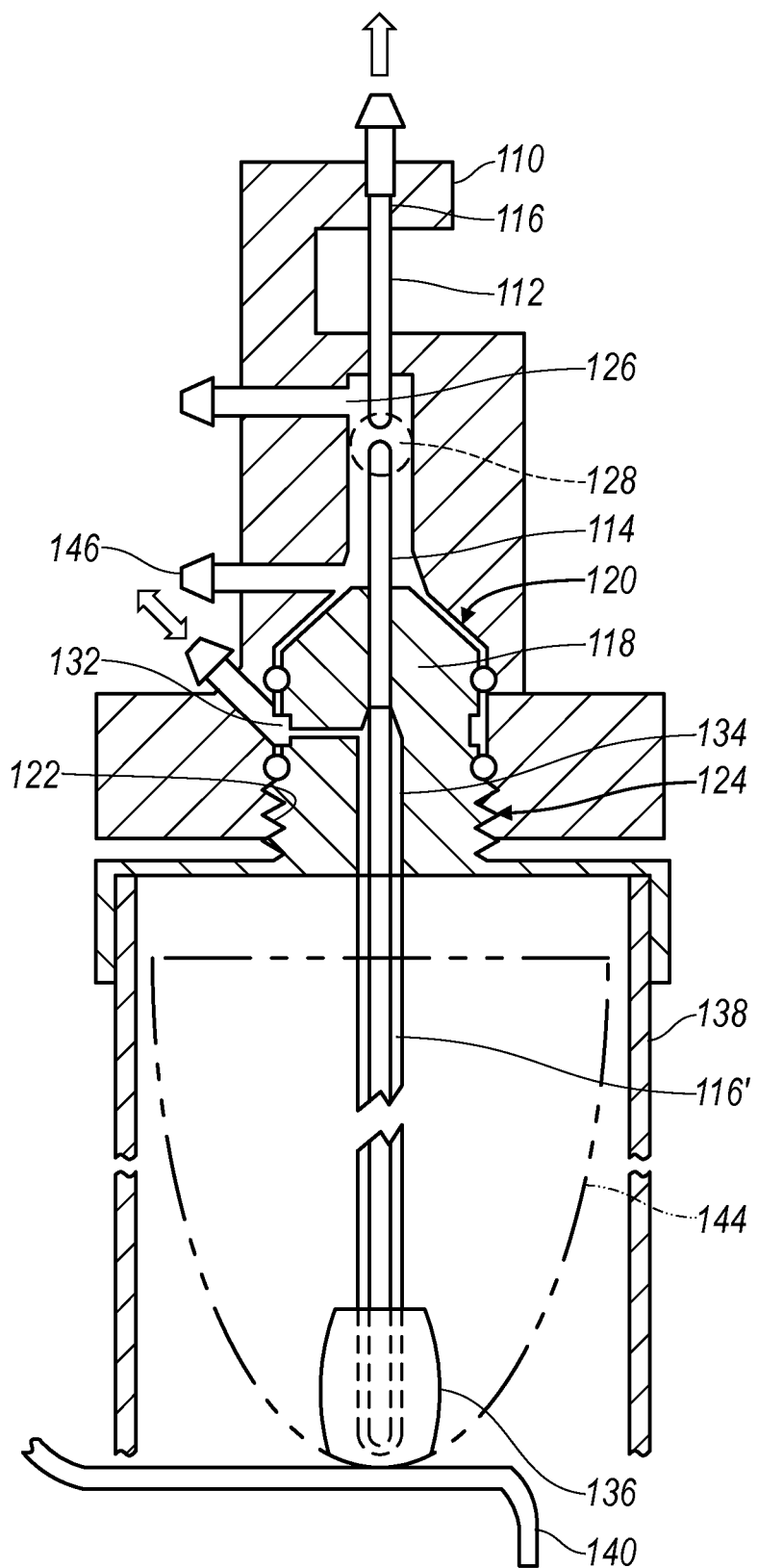
FIG. 1 is a cross section view of a first preferred embodiment of the invention.

As shown in FIG. 1, the flow cytometer system of the preferred embodiment includes a flow cell body 110 that functions to contain, protect, and align the components of the flow cytometer system; a flow channel 112, coupled to the flow cell body 110, that functions to conduct and focus sample fluid through an interrogation zone; and a sample injection probe 114, removably coupled to the flow cell body 110, that functions to provide a uniform flow of sample fluid to the flow channel 112. The flow cytometer system is preferably designed for the flow cytometer field. The flow cytometer system, however, may be alternatively used in any suitable environment and for any suitable reason.

1. Flow Cell Body, Flow Channel, and Sample Injection Probe

The flow cell body 110 of the preferred embodiment functions to contain, protect, and align the components of the flow cytometer system. As shown in FIGS. 1-6, the flow cell body 112 is a unitary construction, which preferably includes a single piece of machined material that contains, protects, and aligns the remaining components of the flow cytometer system, including the flow channel 112. A suitable material for the unitary construction of the flow cell body 110 is polycarbonate, although any suitable metal, plastic, alloy, or composite material can be readily substituted for the unitary construction material.

The flow cell body 110 is preferably manufactured according to methods known in the art of manufacture, including for example CNC machining and injection molding or any combination thereof. The method of manufacture of the flow cell body 110 of the preferred invention includes the steps of providing a material, and disposing a receiving channel 116 in the material such that the receiving channel 116 is appropriately sized for receiving and holding the flow channel 112. Suitable materials include polycarbonate, although any suitable metal, plastic, alloy, or composite material can be readily substituted for material. The receiving channel 116 is preferably manufactured such that it provides an opening through which the flow channel 112 is radially exposed for the interrogation of the samples within the flow channel 112.

Figure 4:
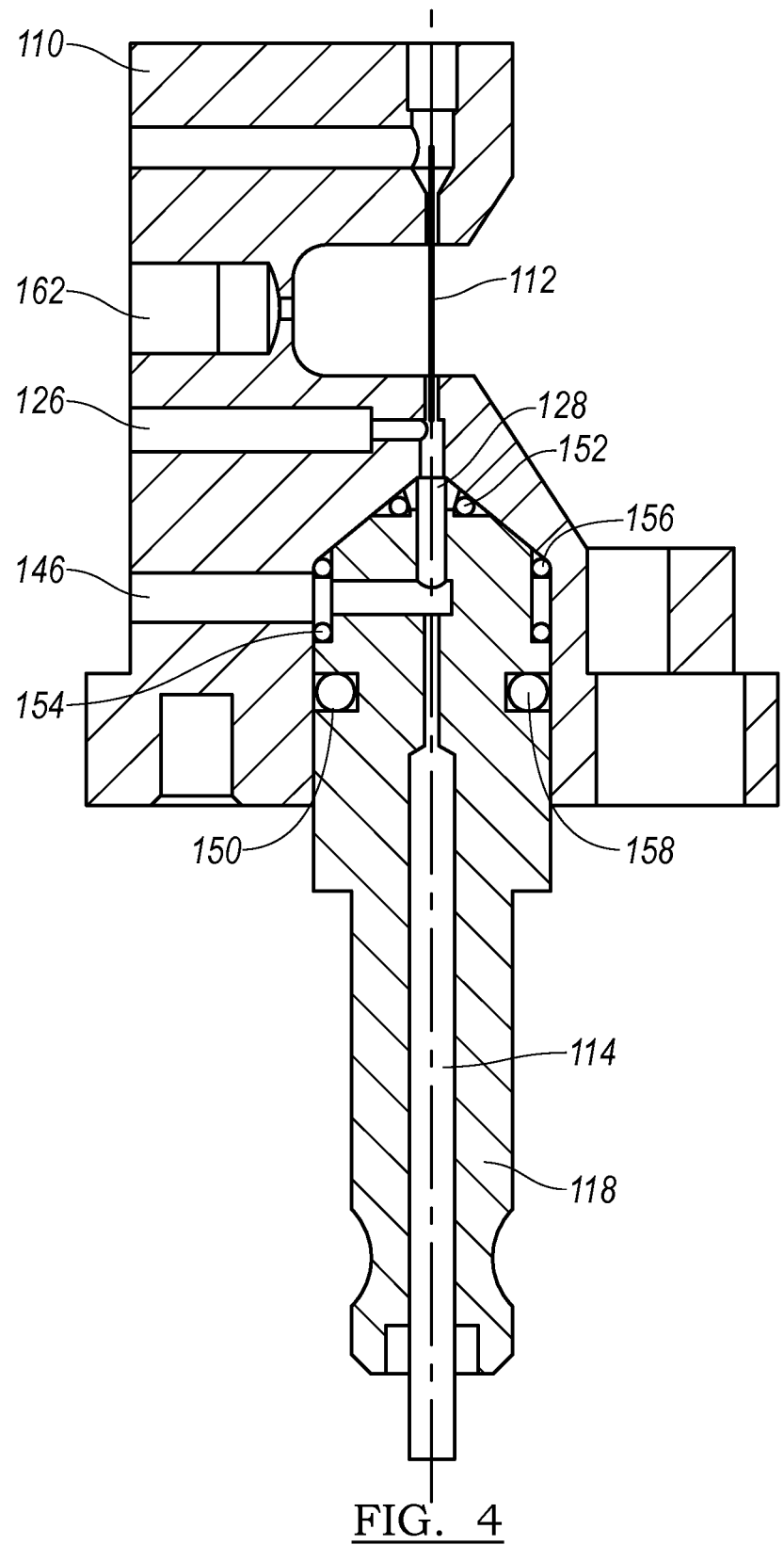
FIGS. 4 and 5 are cross section views of a second preferred embodiment of the invention.

The flow channel 112 of the preferred embodiment is coupled to the flow cell body 110 and functions to conduct and focus sample fluid through an interrogation zone, where the sample material is analyzed. As shown in FIGS. 1 and 4, the flow channel 112 is preferably mounted within the flow cell body 110 and is typically a small passageway, typically less than 0.3 mm in diameter. The flow channel 112 is preferably made from an optical grade fused silica, but may alternatively be made from any suitable material such as suitable optically clear capillary materials. The flow channel preferably has a circular cross section, but may alternatively have any suitable cross section geometry. The sample fluid or sample material may be anything capable of being inserted into the flow path. Sample material may include cells, biological materials, or other particles to be assayed, measured, or counted.

The sample injection probe (SIP) 114 of the preferred embodiment is removably coupled to the flow cell body 110 and functions to provide a uniform flow of sample fluid to the flow channel 112. As shown in FIGS. 1 and 4, the SIP 114 of the preferred embodiment is preferably selectively removable from the flow cell body 110 and includes a small diameter capillary that functions to retrieve the sample fluid from a sample fluid reservoir or sample vial 144 and to pass the sample fluid upstream towards the flow channel 112. The small diameter of the SIP 114 functions to provide a uniform flow of sample fluid to the flow channel 112 and to minimize the injection of gases that may contribute to the formation of bubbles. The SIP 114 preferably has a cross section geometry that is substantially circular, however the cross section geometry may alternatively be any other suitable cross section geometry. The cross section geometry may change geometry or dimension along the length of the SIP 114. As shown in FIG. 4, the portion of the SIP 114 that extends into the sample vial 114 may have a larger diameter than the portion of the SIP 114 that extends towards the flow channel 112. The transition between the various diameters of the SIP 114 may have a shoulder with a small corner radius, as shown in FIG. 4, or may alternatively have any suitable corner radius or the transition may be tapered. The SIP 114 may be constructed of any suitable material, including for example non-corrosive rigid materials such as stainless steel, plastic or composite. The SIP 114 of the variation of the preferred embodiment is constructed of a single unitary piece, which may be fabricated through any known methods such as CNC machining, injection molding, and the like.

In a variation of the preferred embodiment, the flow cytometer system includes a SIP body 118, as shown in FIGS. 1-5. The SIP body 118 is removably coupled to the flow cell body 110 and functions to contain the SIP 114 and align the SIP 114 with the flow channel 112. The SIP body 118 includes a receiving channel 116' preferably for receiving the SIP 114. The receiving channel 116' is preferably appropriately sized for receiving and holding the SIP 114. The receiving channel 116' preferably has a cross section geometry (that may change geometry or dimension along the length of the receiving channel 116') appropriately sized for receiving and holding the SIP 114 and for aligning the SIP 114 with the flow channel 112. The receiving channel 116' may be dimensioned such that the SIP 114 extends into the flow cell body 110, as shown in FIG. 1, or the receiving channel 116' may be dimensioned such that the SIP 114 remains in the SIP body 118, as shown in FIG. 4. The receiving channel 116' may removably and selectively receiving the SIP 114. Alternatively, the SIP 114 may be coupled to the SIP body 118, and the SIP body 118 is then removably and selectively coupled to the flow cell body 110. The SIP body 118 further includes a mating interface 120 for mating to the flow cell body 110. The mating interface 120 can include a tapered or conical geometry that is configured for precision alignment with the flow cell body 110 thus ensuring proper alignment of the SIP 114 and the flow channel 112. The mating interface can also include a threaded face 122 that complements a threaded receiver 124 on the flow cell body 110, thus providing for regular and precise mating of the SIP body 118 and the flow cell body 110 without the use of specialized tools.

The SIP body 118 may further define a circumferential groove 150 that functions to hold a back-up o-ring 158, or any other suitable element that will increase friction between the SIP body 118 and the flow cell body 110 at a point, that functions to create a seal and/or to create a removable press fit connection between the flow cell body 110 and the SIP body 118. The flow cytometer system may further include a plurality of o-rings. As shown in FIG. 4, the connection between the SIP body 118 and the flow cell body 110 may utilize at least one of a top o-ring 152, a first o-ring 154, a second o-ring 156, and the back-up o-ring 158. The top o-ring 152 preferably functions to seal the top of the SIP body 118 to the flow cell body 110, the first o-ring 154 preferably functions to seal the connection between the input channels 146 of the flow cell body 110 and the SIP body 118, and the second o-ring 156 preferably functions to balance the forces created by the first o-ring.

2. Assembly of the Flow Cytometer System

To ensure accurate analysis of the sample material, the flow channel 112 is preferably correctly aligned with the flow cell body 110. Due to the small size of the flow channel 112 (it is typically a capillary tube less than 0.3 mm in diameter), it is difficult to accurately radially align the capillary tube with the flow cell body 110 during assembly of the flow cell for a flow cytometer system. The flow cytometer is preferably assembled by a method with a device that facilitates the radial alignment of a capillary tube in a flow cell. The device is preferably the assembly fixture 10 of the preferred embodiments, but may alternatively be any suitable device used in any suitable method.

Figure 9:
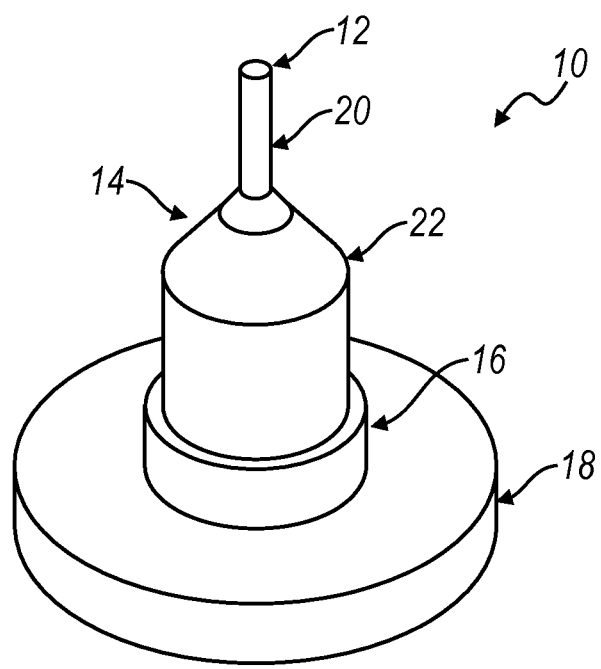
FIG. 9 is a perspective view of a preferred embodiment of the assembly fixture.

As shown in FIG. 9, the assembly fixture 10 of the preferred embodiments defines a capillary receptacle 12 adapted to receive a capillary tube for assembly, defines an alignment element 14 adapted to align the assembly fixture 10 with the flow cell body 110, and includes a coupling element 16 adapted to removably couple the assembly fixture 10 with a flow cell body 110. The assembly fixture 10 is, in some respects, a "golden tool" that facilitates a relaxed tolerance for the original bore for the capillary tube and facilitates accurate alignment in a faster, cheaper, reproducible manner. The assembly fixture 10 is preferably designed to facilitate the assembly of a flow cell and, more specifically, to properly radially align a capillary tube within a flow cell of a flow cytometer. The assembly fixture 10, however, may be alternatively used in any suitable environment and for any suitable reason.

The assembly fixture 10 of the preferred embodiments is an article of manufacture, preferably made out of a metal such as brass. The assembly fixture 10 may alternatively be made out of any suitable rigid material such as stainless steel, plastic or composite. The assembly fixture is preferably constructed of a single unitary piece, which may be fabricated through any known methods such as CNC machining, injection molding, and the like.

Figure 10:
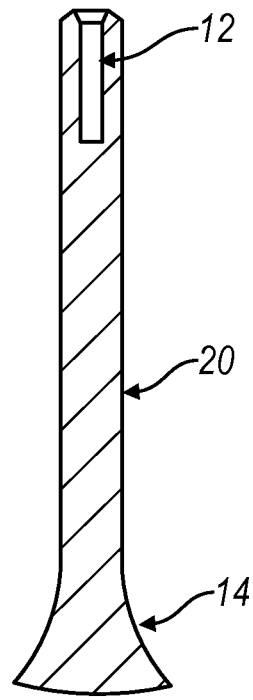
FIG. 10 is an enlarged perspective view of the capillary receptacle and alignment element of the preferred embodiment.

The capillary receptacle 12 of the preferred embodiments functions to receive a capillary tube for assembly. As shown in FIG. 10, the capillary receptacle 12 is preferably located at the top portion of the assembly fixture 10. The capillary receptacle 12 is preferably precision machined and or ground, but may alternatively be made in any suitable method to ensure accurate dimensions for the proper radial alignment of the capillary tube. The capillary receptacle 12 preferably has a cross section geometry and a depth. The cross section geometry is preferably substantially circular, such that the capillary tube fits into the receptacle and is radially aligned by the walls of the receptacle. The cross section geometry may alternatively be any suitable cross section geometry such that the capillary receptacle 12 receives and radially aligns a capillary tube. Additionally, the cross section geometry may change geometry or dimension along the length of the receptacle. Preferably, the cross section geometry is dimensioned such that the capillary tube will be radially aligned and therefore properly positioned with the flow cell body 110 upon assembly. The capillary receptacle 12 preferably has a depth such that a portion of the capillary tube remains exposed beyond the assembly fixture 10. The exposed portion of the capillary tube is preferably the portion of the capillary tube that couples to the flow cell body 110. Preferably, the depth is dimensioned such that the capillary tube will be axially aligned and therefore properly positioned with the flow cell body 110. The capillary tube is preferably coupled to the flow cell body 110 with adhesive, but may alternatively be connected by any other suitable material or suitable methods.

Figure 11:
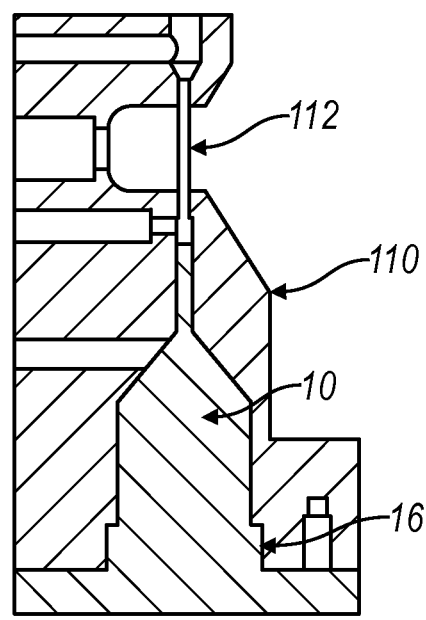
FIG. 11 is a cross sectional view of the assembly fixture coupled to the flow cell body.

As shown in FIGS. 9, 10, and 11, the alignment element 14 of the preferred embodiments functions to align the assembly fixture 10 with the flow cell body 110. The alignment element 14 includes a mating interface that functions to mate the assembly fixture 10 and the flow cell body 110. The mating interface includes a geometry and dimensions that are configured for precision alignment with the flow cell body 110 thus ensuring proper radial and axial alignment of the assembly fixture 10 and the capillary tube. The mating interface is preferably precision machined and or ground, but may alternatively be made in any suitable method to ensure proper alignment geometry and dimensions.

The alignment element 14 preferably includes at least one of a nozzle region mating interface 20 and SIP body mating interface 22. The nozzle region mating interface 20 is preferably located at the top portion of the assembly fixture 10 and is substantially cylindrically shaped. The nozzle region mating interface 20 is preferably dimensioned such that it fits tightly with the flow cell nozzle region of the flow body. The SIP body mating interface 22 is preferably a tapered or conical geometry that is configured for precision alignment with the portion of the flow cell body 110 with which the SIP body mating interface 120 aligns. The dimensions of the SIP body mating interface 22 are preferably the same or similar to the mating interface 120 of the SIP body 118. The use of a tapered or conical geometry assures both a particular radial and axial mating between the flow cell and the assembly fixture. Other suitable dimensions may, however, be used.

The coupling element 16, as shown in FIG. 9, of the preferred embodiments functions to removably mount the assembly fixture 10 with a flow cell body 110. Additionally, the coupling element 16, with the alignment element 14, functions to radially and axially align the assembly fixture 10 with the flow cell body 110. Preferably, the coupling element 16 is one of several variations. In a first variation, as shown in FIG. 9, the coupling element 16 is a threaded face (exterior threads) that complements a threaded receiver (interior threads) on the flow cell body 110, thus providing for regular and precise mating of the assembly fixture 10 and the flow cell body 110 without the use of specialized tools. In a second variation, the coupling element is a friction coupling element, preferably an o-ring. In this variation, the assembly fixture 10 preferably defines a circumferential groove that functions to hold an o-ring or any other suitable element that will increase friction between the assembly fixture 10 and the flow cell body 110 at a point to create a removable press fit connection and/or to create a seal. The coupling element 16 may, however, utilize any other suitable means for removably coupling the assembly fixture 10 with the flow cell body 110.

The assemble fixture 10 of the preferred embodiment may further include a handle 18, as shown in FIGS. 9 and 11. The handle 18 of the preferred embodiments functions to provide a gripping surface used to couple and uncouple the assembly fixture 10 from the flow cell body 110. The handle 18 is preferably located at the bottom portion of the assembly fixture 10 and preferably at least a portion of the handle 18 remains exposed beyond the flow cell body 110 when the assembly fixture 10 is coupled to the flow cell body 110. The handle 18 is preferably cylindrically shaped and dimensioned such that the outer diameter of the handle is at least the size of the flow cell body 110. The handle 18 may alternatively be any other suitable shape or size to provide an accessible gripping surface. Additionally, the handle 18 may be knurled or include a grip material such as rubber, such that the handle is easily grasped and manipulated.

The assembly fixture 10 of the preferred embodiments is preferably used to assemble a flow cell. The method of assembling the flow cytometer system of the preferred embodiments includes providing a flow cell body 110, a capillary tube (flow channel 112), and an assembly fixture 10; coupling the capillary tube to the assembly fixture 10 in the capillary receptacle 12 of the assembly fixture 10; coupling the assembly fixture 10 to the flow cell body 110 and attaching the capillary tube to the flow cell body 110; and removing the assembly fixture 10 from the flow cell body 110. The method is preferably designed for the assembly of the flow channel 112 and the flow cell body 110 of the preferred embodiments. The method, however, may be alternatively used in any suitable environment and for any suitable reason.

The step that recites providing a flow cell body 110, a capillary tube (flow channel 112), and an assembly fixture 10, functions to provide the elements of the flow cytometer system that will be coupled together. The step that recites coupling the capillary tube to the assembly fixture 10 in the capillary receptacle 12 of the assembly fixture 10, functions to place the capillary tube in the capillary receptacle such that the capillary tube is radially aligned by the walls of the receptacle and a portion of the capillary tube remains exposed beyond the assembly fixture 10 and is axially aligned.

The step that recites coupling the assembly fixture 10 to the flow cell body 110 and attaching the capillary tube to the flow cell body 110, functions to couple the assembly fixture 10 with the correctly aligned capillary tube into the flow cell body 110, as shown in FIG. 11. The alignment element 14 of the assembly fixture 10 will properly align the assembly fixture 10 with the flow cell body 110 and therefore, the radially and axially aligned capillary tube will be guided into the correct portion of the flow cell body 110. The coupling element 16 of the assembly fixture 10 may be coupled with the flow cell body 110 ensuring proper position and alignment of the capillary tube within the flow cell body 110. Once the assembly fixture 10 is coupled to the flow cell body 110, the capillary tube is preferably attached to the flow cell body 110 with an adhesive or any other suitable device or method.

The step that recites removing the assembly fixture 10 from the flow cell body 110, functions to uncouple the coupling element 16 and remove the assembly fixture 10, leaving a properly assembled capillary tube in place within the flow cell body 110.

Although omitted for conciseness, the preferred embodiments include every combination and permutation of the assembly fixture 10, the capillary receptacle 12, the alignment element 14, the coupling element 16, the handle 18, and any method of assembling the capillary tube within a flow cell body 110 using the assembly fixture 10.

3. Other Aspects of the Invention

In a variation of the preferred embodiment, the flow cytometer system includes a bubble purge port 126, as shown in FIGS. 1-5. The bubble purge port 126 is connected to the flow cell body 110 upstream from (before) the interrogation zone and is fluidically coupled to the sample fluid flowing through the flow cell body 110. The bubble purge port 126 functions to selectively purge bubbles prior to their entry into the flow channel 112, thus preventing substantially all bubbles from interfering with the data collection in the interrogation zone. The bubble purge port 126 also functions to selectively clear sample debris, conjugated or clustered cells, or other substances from the nozzle region or hydrodynamic focusing region 128. The bubble purge port 126 may be located upstream or downstream from the hydrodynamic focusing region 128, as shown in FIGS. 1 and 4 respectively. The bubble purge port 126 can be operated manually by a user during operation of the flow cytometer. Alternatively, the bubble purge port 126 can be automated and adapted to respond to signals from a bubble detector adapted to detect the presence of bubbles approaching the flow channel 112.

In another variation of the preferred embodiment, the flow cytometer system includes a hydrodynamic focusing region 128, as shown in FIGS. 1-4. The hydrodynamic focusing region 128 is connected to the flow channel 112 and adapted to pass sample fluids into the flow channel 112 for interrogation. The hydrodynamic focusing region 128 preferably includes a nozzle having a substantially cylindrical body that is configured to receive a sample fluid and a sheath fluid, but may alternatively include any suitable device or method. The sheath fluid is pumped into the nozzle to focus the sample fluid into a core for passage through the flow channel 112. The sheath fluid is preferably pumped into the nozzle from an input channel 146, as shown in FIGS. 1-5. As the interaction between the sheath fluid and the sample fluid may cause bubbles, the nozzle is preferably disposed within the flow cytometer upstream of the bubble purge port 126 in thus permitting the purging of bubbles related to the focusing process.

Figure 2:
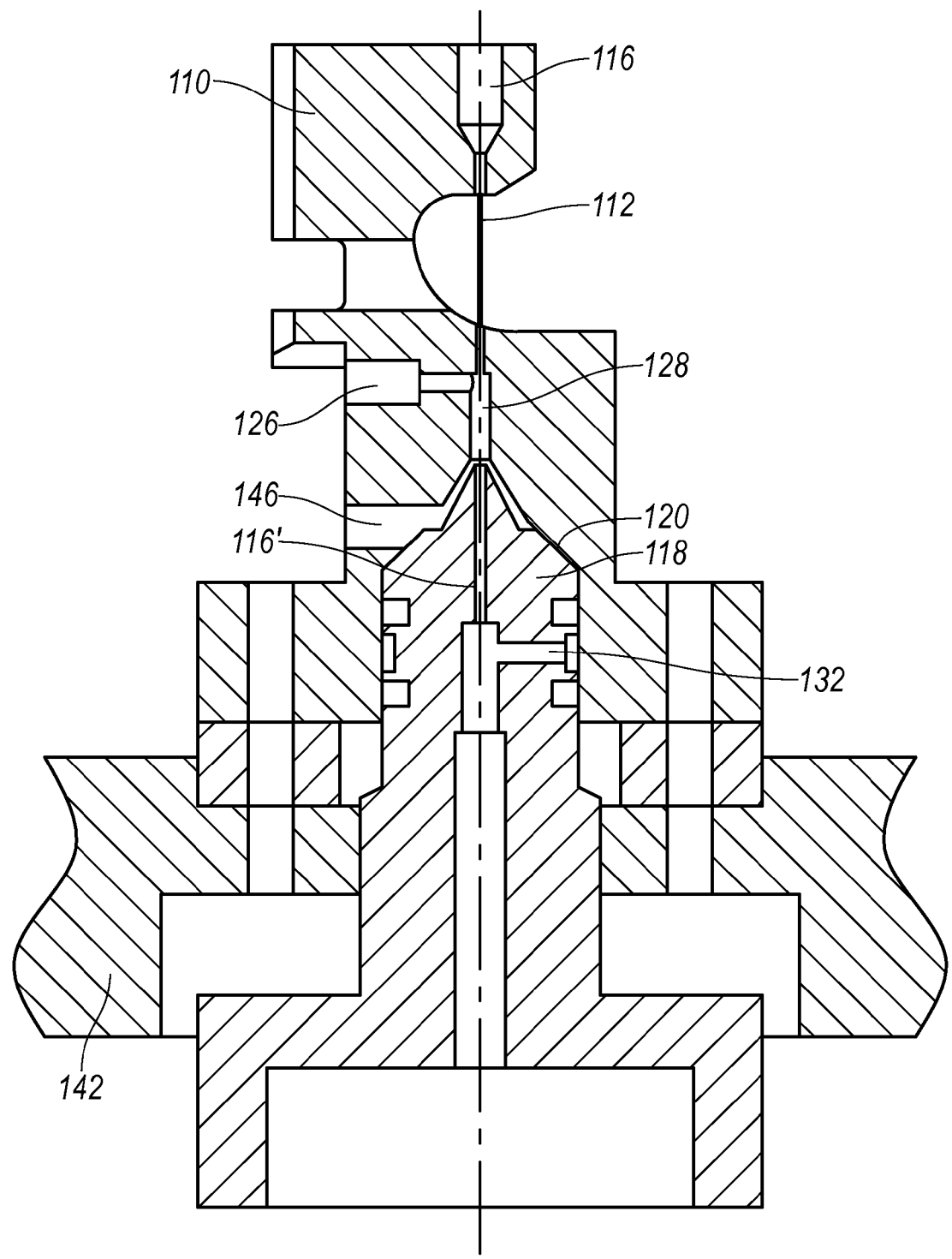
FIGS. 2 and 3 are a side and perspective view, respectively, of a cross section of a variation of a first preferred embodiment of the invention.
Figure 3:
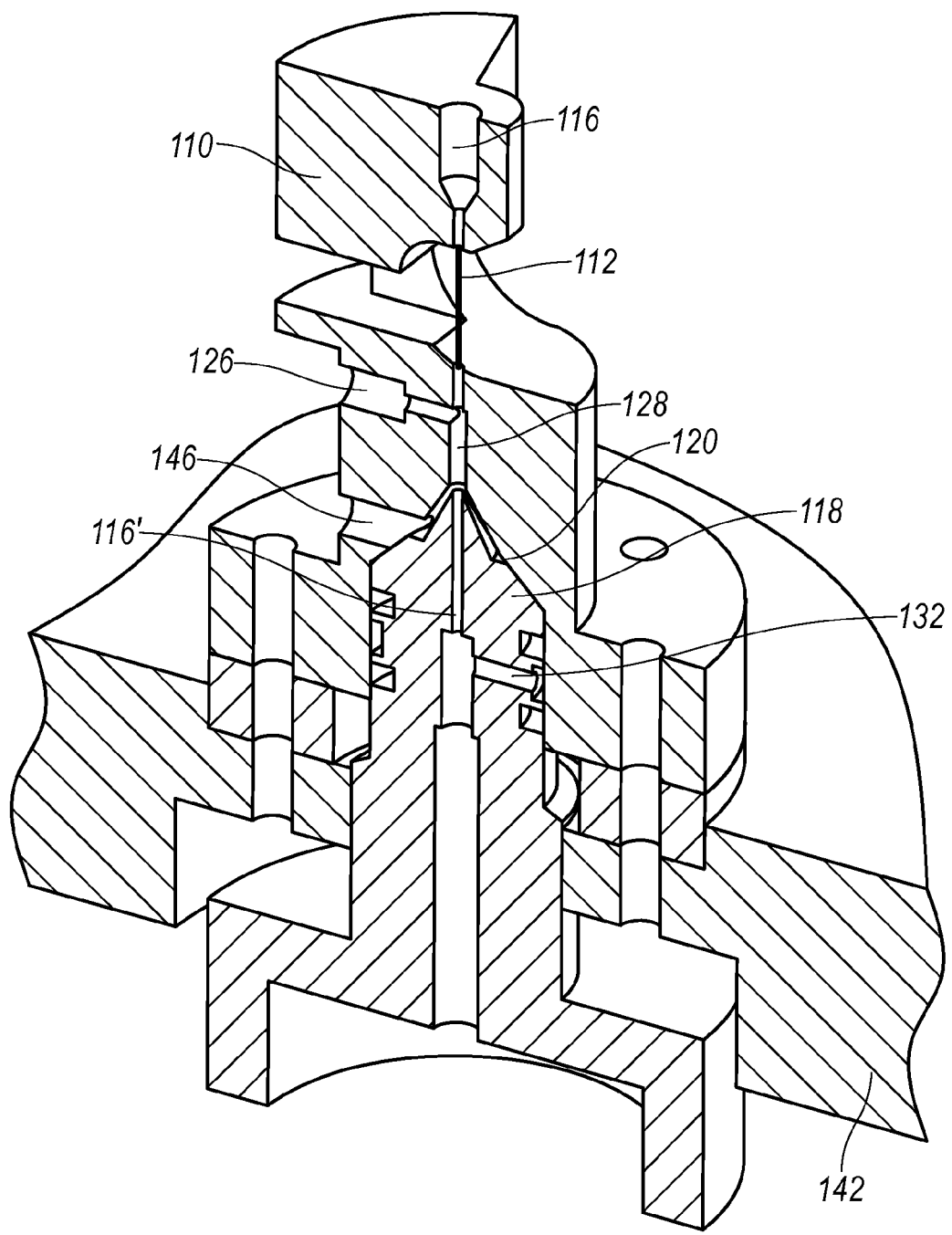

In another variation of the preferred embodiment, the flow cytometer includes a SIP cleaning port 132, as shown in FIGS. 1-3. The SIP cleaning port is preferably connected to a portion the SIP body 118 and is preferably in fluidic communication with the SIP 114. The SIP cleaning port 132 functions to allow a user to relieve pressure from the SIP 114 and also to clean the SIP 114 by introducing sheath fluid therein. The SIP cleaning port 132 can also be connected within a portion of the flow cell body 110 such that the SIP cleaning port 132 is accessible through both the flow cell body 110 and the SIP body 118 thus allowing a user to use the SIP cleaning port 132 while the flow cytometer is fully assembled or in operation. As such, the SIP body 118 and the flow cell body 110 can be configured with passages through which the SIP cleaning port 132 can pass while remaining in fluidic communication with the SIP 114 and being accessible to the user.

In another variation of the preferred embodiment, the flow cytometer includes a pressure monitoring tube 134, as shown in FIG. 1. The pressure monitoring tube 134 is a sheath tube concentrically located about the SIP 114 in a substantially symmetrical manner. The pressure monitoring tube 134 functions to monitor the pressure within the SIP 114 to ensure that the influx of sample fluid is optimized for the introduction of the sheath fluid and the testing of the sample in the flow channel 112. The pressure monitoring tube 134 can be connected to the SIP cleaning port 132 thus permitting the substantially synchronized recognition of pressure in the SIP 114 and its release through the SIP cleaning port 132.

In another variation of the preferred embodiment, the flow cytometer includes a SIP filter 136, as shown in FIG. 1. The SIP filter 136 is connected at an upstream end of the SIP 114 substantially adjacent to the sample reservoir or sample vial 144. The SIP filter 136 functions to substantially remove any large or obtrusive particles prior to entry into the SIP 114 and the flow channel 112, thus reducing the probability of any clogs during operation of the flow cytometer. The SIP filter 136 can include a porous medium such as a synthetic fabric, polymer or composite weave, or metallic mesh having a predetermined pore size for filtering out particles having a selected diameter. In other embodiments, the flow cytometer can include more than one SIP filter 136, each of which can have substantially identical or substantially different pore sizes for providing redundancy in the filtering process.

In another variation of the preferred embodiment, the flow cytometer includes a sample vial mechanism 138, as shown in FIG. 1. The sample vial mechanism 138 functions to selectively hold and accurately align a sample vial 144 with the SIP 114. The sample vial mechanism 138 can be integrated into the SIP body 118, thus rendering it selectively connectable to the flow cell body 110. Alternatively, the sample vial mechanism 138 can be selectively connected to the SIP body 118. The sample vial mechanism 138 functions to properly align the sample vial 144 (which may be sealed and pressurized) with the SIP 114 for removal to the flow channel 112. The sample vial mechanism 138 includes a substantially cylindrical body portion that receives a substantially cylindrical sample vial 144. The sample vial mechanism 138 also includes a release mechanism 140 that allows a user to secure the sample vial 144 within the body portion and in communication with the SIP 114. The release mechanism 140 is configured such that the sample vial 144, when inserted or removed from the body portion, is limited in its movement to a single degree of freedom that is substantially parallel to the SIP 114, thus preventing any shearing, torquing or other damaging forces on the SIP 114 itself.

Figure 5:
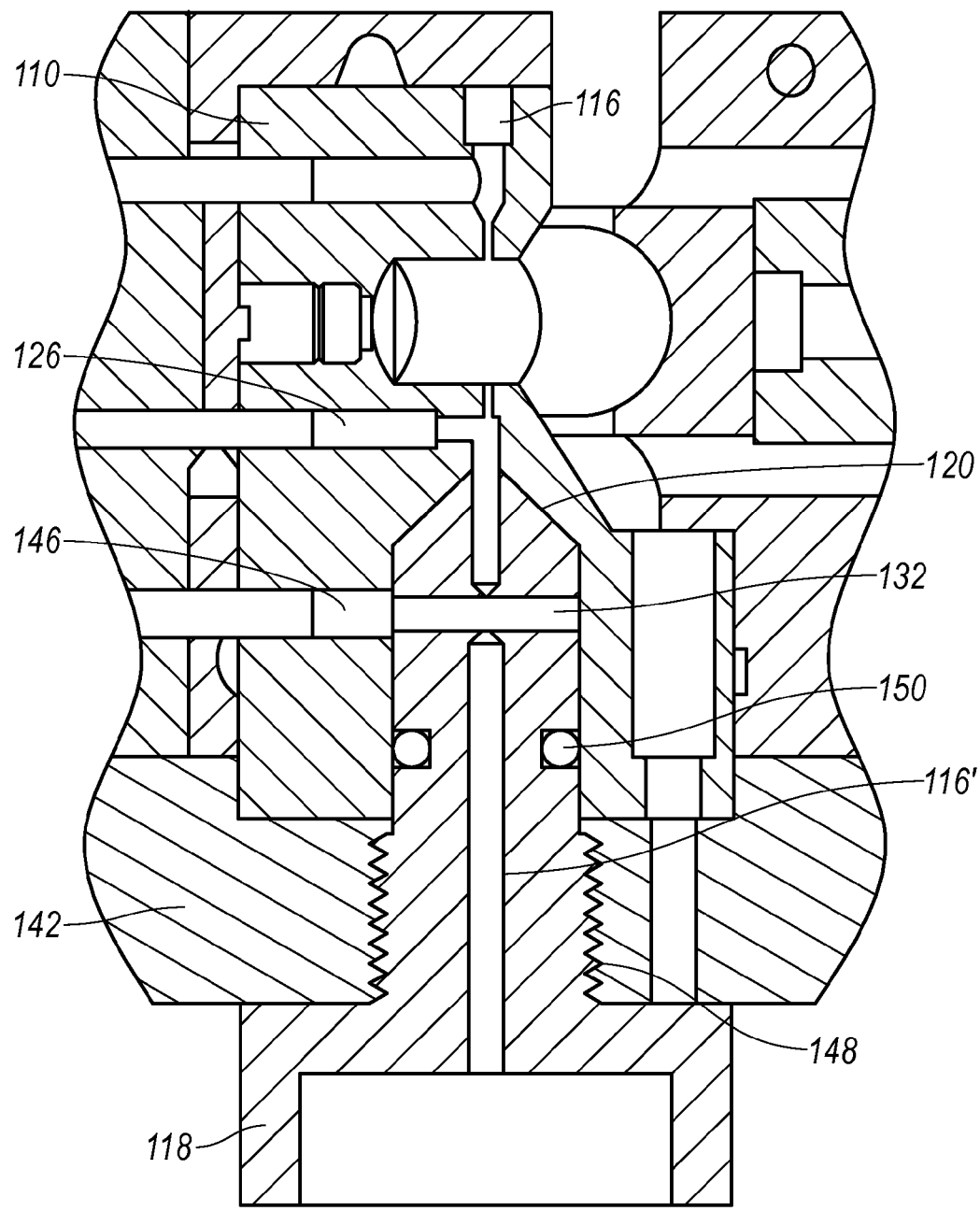
Figure 7:
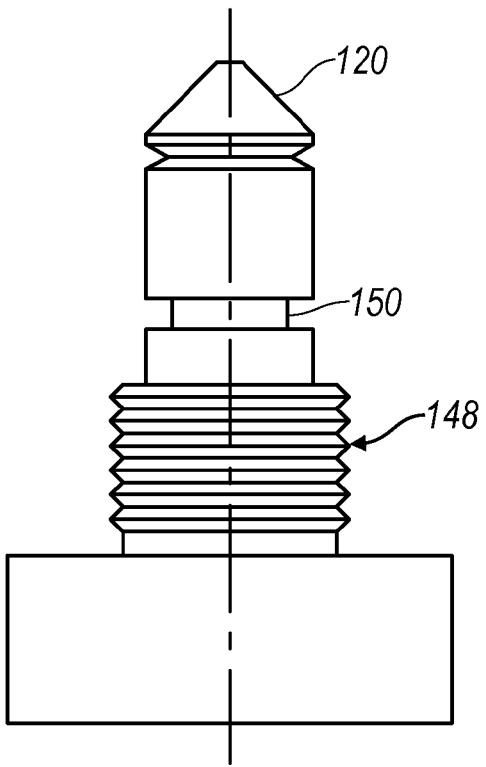
FIGS. 7 and 8 are a side and a cross section view, respectively, of the sample injection probe body of a second preferred embodiment of the invention.
Figure 8:
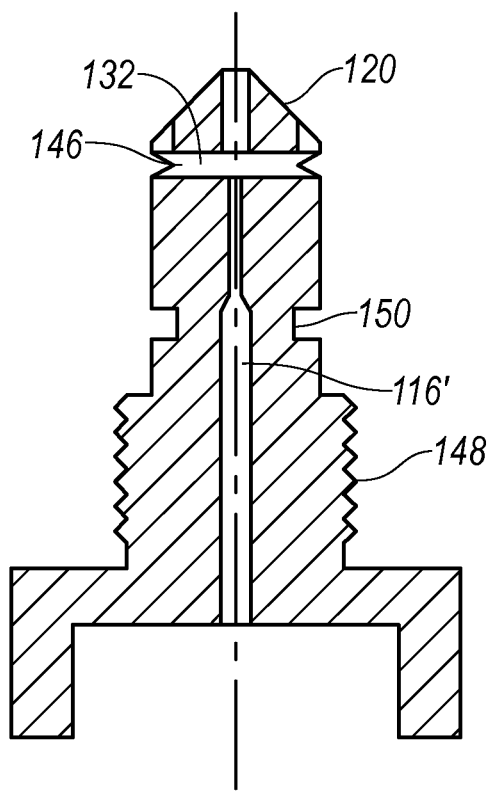

In another variation of the preferred embodiment, as shown in FIGS. 2, 3 and 5, the flow cytometer also includes a base plate 142. In this variation, the flow cell body 110 is preferably mounted to the base plate 142 with screws or other suitable fasteners, while the SIP body 118 is preferably mounted to the base plate 142 through a threaded interface or other suitable method or device. As shown in FIGS. 5, 7, and 8, the SIP body includes a threaded face 148 that complements a threaded receiver on the base plate. The use of the base plate 142 may reduce stress on the flow cell while still using a cone-in-cone fit to align the SIP 114 to the flow cell capillary.

Figure 6:
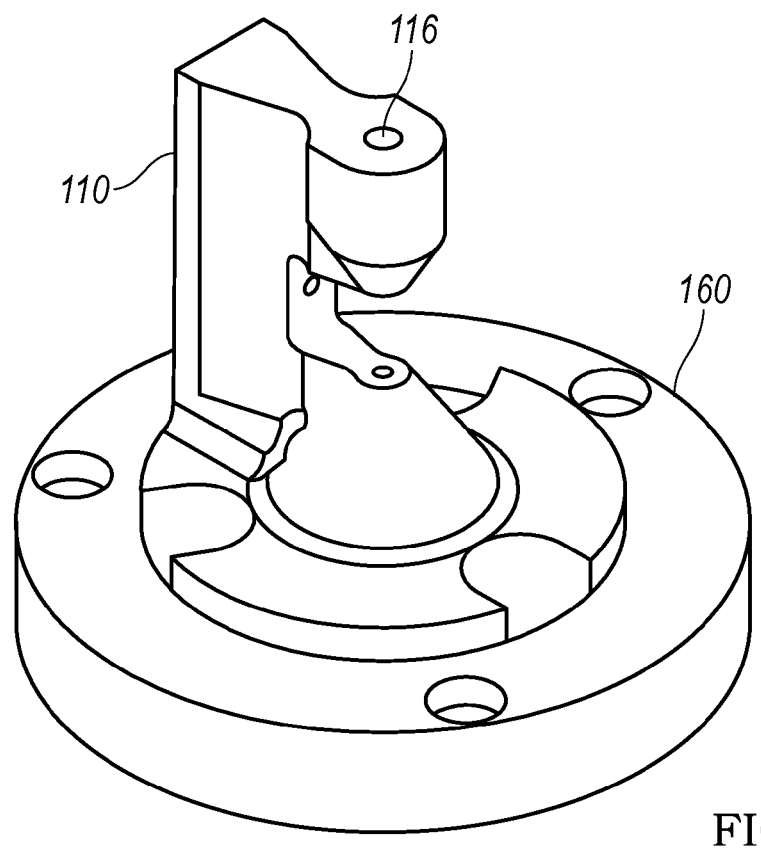
FIG. 6 is a perspective view of the flow cell body of a second preferred embodiment of the invention.

In another variation of the preferred embodiment, as shown in FIG. 6, the flow cytometer also includes a retaining ring 160. The retaining ring 160, coupled to the flow cell body 110, that functions to apply an evenly distributed pressure around the diameter of the flow cell body 110 during assembly and use. The retaining ring 160 further functions as an alignment aid, providing a guide to precisely rotate the flow cell body. The retaining ring is preferably made from any suitable metal, plastic, rubber, alloy, or composite material.

In another variation of the preferred embodiment, as shown in FIG. 4, the flow cytometer also includes a lens 162. The lens 162 is preferably coupled to the flow cell body 110 adjacent to the interrogation zone and functions to focus an illumination source that impinges the interrogation zone. The illumination source is preferably a laser, but may alternatively be any suitable illumination source.

As a person skilled in the art of flow cytometry will recognize from the previous detailed description and from the figures and claim, modifications and changes can be made to the preferred embodiments of the invention without departing from the scope of this invention defined in the following claim.

We claim:

1. A flow cytometer system having an interrogation zone, the flow cytometer system comprising:
    a flow cell body that is a unitary construction and that contains and aligns components of the flow cytometer system;
    a focusing lens, coupled to and located within the flow cell body adjacent to the interrogation zone, configured to focus light that impinges the interrogation zone;
    a flow channel, coupled to the flow cell body, that conducts and focuses sample fluid through the interrogation zone;

a sample injection probe, removably coupled to the flow cell body, that provides a sample fluid to the flow channel;

a sample injection probe body, removably coupled to the flow cell body, that contains the sample injection probe and aligns the sample injection probe with the flow channel;

a sample injection probe cleaning port, at least partially defined within the sample injection probe body and fluidically coupled to the sample injection probe, that is configured to relieve pressure from the sample injection probe and configured to clean the sample injection probe by introducing sheath fluid therein; and a bubble purge port fluidically coupled to the flow cell body and defined in the flow cell body upstream from the interrogation zone for a flow direction from the sample injection probe to the interrogation zone, wherein the bubble purge port is configured to selectively purge bubbles prior to their entry into the flow channel.

2. The flow cytometer system of claim 1 wherein the flow cell body includes a receiving channel that receives and holds the flow channel and provides an opening through which the flow channel is radially exposed for an interrogation of the sample fluid within the flow channel.

3. The flow cytometer system of claim 1 wherein the flow channel is mounted within the flow cell body and is a small diameter capillary made from an optically clear material.

4. The flow cytometer system of claim 1 wherein the sample injection probe is a small diameter capillary made from a unitary piece of non-corrosive rigid material.

5. The flow cytometer system of claim 1 wherein the sample injection probe body includes a mating interface for mating to the flow cell body.

6. The flow cytometer system of claim 5 wherein the mating interface includes a conical geometry that is configured for alignment of the sample injection probe body with the flow cell body.

7. The flow cytometer system of claim 5 wherein the sample injection probe body defines a circumferential groove that holds an o-ring, wherein the o-ring creates a seal and removably couples the sample injection probe body with the flow cell body.

8. The flow cytometer system of claim 1 wherein the bubble purge port selectively clears debris prior to entry into the flow channel for the flow direction from the sample injection probe to the interrogation zone.

9. The flow cytometer system of claim 1 further comprising a hydrodynamic focusing region, connected to the flow channel, that passes sample fluids into the flow channel for interrogation, wherein the hydrodynamic focusing region includes a nozzle, having a substantially cylindrical body, that is adapted to receive a sample fluid and a sheath fluid.

10. The flow cytometer system of claim 1 wherein the sample injection probe cleaning port is further connected to the flow cell body.

11. The flow cytometer system of claim 1 further comprising a pressure monitoring tube, concentrically located about the sample injection probe in a substantially symmetrical manner, that monitors the pressure within the sample injection probe.

12. The flow cytometer system of claim 11 wherein the pressure monitoring tube is connected to a sample injection probe cleaning port, such that the recognition of pressure in the sample injection probe and release of the pressure in the sample injection probe through the sample injection probe cleaning port is substantially synchronized.

13. The flow cytometer system of claim 1 further comprising a sample vial and a sample vial mechanism, wherein the sample vial mechanism selectively holds and accurately aligns the sample vial with the sample injection probe.

14. The flow cytometer system of claim 13 further comprising a sample injection probe filter, connected at an upstream end of the sample injection probe and substantially adjacent to the sample vial, that substantially removes debris prior to entry into the sample injection probe and the flow channel, wherein the sample injection probe filter includes a porous medium having a predetermined pore size for filtering out particles having a selected diameter.

15. The flow cytometer system of claim 1 further comprising a base plate, wherein the flow cell body and the sample injection probe body are mounted to the base plate.

16. The flow cytometer system of claim 15 wherein the sample injection probe body further includes a threaded face and the base plate further includes a complimentary threaded receiver, wherein the threaded face and the threaded receiver are configured for mating of the sample injection probe body and the base plate.

17. The flow cytometer system of claim 1 further comprising a retaining ring, coupled to the flow cell body, that applies a substantially evenly distributed pressure around the diameter of the flow cell body.

18. The flow cytometer system of claim 1 wherein the bubble purge port is approximately orthogonal to the longitudinal axis of the flow channel.

19. A flow cytometer system having an interrogation zone, the flow cytometer system comprising:

a flow cell body that is a unitary construction and that contains and aligns components of the flow cytometer system;

a focusing lens, coupled to and located within the flow cell body adjacent to the interrogation zone, configured to focus light that impinges the interrogation zone;

a flow channel, coupled to the flow cell body, that conducts and focuses sample fluid through the interrogation zone;

a sample injection probe, removably coupled to the flow cell body, that provides a sample fluid to the flow channel;

a sample injection probe body, removably coupled to the flow cell body, that aligns the sample injection probe with the flow channel; and a sample injection probe cleaning port, at least partially defined within the sample injection probe body and fluidically coupled to the sample injection probe, that is configured to relieve pressure from the sample injection probe and configured to clean the sample injection probe by introducing sheath fluid therein.

* * * * *